United States Patent [19]

Martakos et al.

[11] Patent Number: 5,433,909
[45] Date of Patent: Jul. 18, 1995

[54] METHOD OF MAKING CONTROLLED POROSITY EXPANDED POLYTETRAFLUOROETHYLENE PRODUCTS

[75] Inventors: Paul Martakos, Pelham; Theodore Karwoski, Hollis; Steve A. Herweck, Nashua, all of N.H.

[73] Assignee: Atrium Medical Corporation, Hudson, N.H.

[21] Appl. No.: 31,238

[22] Filed: Mar. 12, 1993

Related U.S. Application Data

[63] Continuation-in-part of Ser. No. 850,862, Mar. 13, 1992.

[51] Int. Cl.⁶ .................................................. B29C 55/00
[52] U.S. Cl. .................................. 264/209.1; 264/127; 264/288.8; 264/289.3
[58] Field of Search ............... 264/288.8, 241, 127, 264/289.3, 300, 41, 177.14, 209.1; 428/36.5, 36.9; 623/1

[56] References Cited

U.S. PATENT DOCUMENTS

| | | | |
|---|---|---|---|
| Re. 31,618 | 7/1984 | Mano et al. | 3/1.4 |
| 2,915,786 | 12/1959 | Haroldson et al. | 18/55 |
| 2,953,428 | 9/1960 | Hunt et al. | 18/54 |
| 3,054,761 | 9/1962 | Moore et al. | 260/2.5 |
| 3,094,762 | 6/1963 | Jackel | 28/72 |
| 3,198,691 | 8/1965 | Thomas et al. | 161/184 |
| 3,231,460 | 1/1966 | Andrews | 161/189 |
| 3,265,092 | 8/1966 | Ely, Jr. et al. | 138/118 |
| 3,322,608 | 5/1967 | Mason et al. | 161/87 |
| 3,365,355 | 1/1968 | Netsch | 161/116 |
| 3,407,249 | 10/1968 | Landi | 264/49 |
| 3,473,087 | 10/1969 | Slade | 317/2 |
| 3,486,961 | 12/1969 | Adams | 156/306 |
| 3,513,064 | 5/1970 | Westley | 161/92 |
| 3,544,671 | 12/1970 | Sandiford | 264/210 |
| 3,634,564 | 1/1972 | Okamoto et al. | 264/54 |
| 3,637,906 | 1/1972 | Le Parathoën | 260/857 |
| 3,664,915 | 5/1972 | Gore | 161/164 |
| 3,783,057 | 1/1974 | McNerney | 156/49 |
| 3,813,461 | 5/1974 | Murayama et al. | 264/41 |
| 3,887,761 | 6/1975 | Gore | 174/110 |
| 3,953,566 | 4/1976 | Gore | 264/235.6 |
| 3,962,153 | 7/1976 | Gore | 260/2.5 |
| 3,974,526 | 8/1976 | Dardik et al. | |
| 4,031,283 | 6/1977 | Fagan | 423/280 |
| 4,061,134 | 12/1977 | Samuels et al. | 128/1 |
| 4,082,893 | 4/1978 | Okita | 428/376 |
| 4,096,227 | 6/1978 | Gore | 264/210 |
| 4,104,394 | 8/1978 | Okita | 264/89 |
| 4,113,912 | 9/1978 | Okita | 428/290 |
| 4,177,334 | 12/1979 | Okita | 521/145 |
| 4,187,390 | 2/1980 | Gore | 174/102 |
| 4,193,138 | 3/1980 | Okita | 623/1 |
| 4,208,745 | 6/1980 | Okita | 264/289.3 |
| 4,209,480 | 6/1980 | Homsy | 264/108 |
| 4,225,547 | 9/1980 | Okita | 264/127 |
| 4,234,535 | 11/1980 | Okita | 264/288.8 |
| 4,250,138 | 2/1981 | Okita | 264/568 |
| 4,277,429 | 7/1981 | Okita | 264/127 |
| 4,303,714 | 12/1981 | Mercer | 428/135 |
| 4,304,010 | 12/1981 | Mano | 3/1.4 |
| 4,309,776 | 1/1982 | Berguer | 3/1 |

(List continued on next page.)

*Primary Examiner*—Allan R. Kuhns
*Attorney, Agent, or Firm*—Lahive & Cockfield

[57] ABSTRACT

A method of forming porous articles with a varying pore distribution by extrusion from a billet with a varying lubricant distribution. A single-polymer polytetrafluoroethylene is extruded and then stretched and sintered to provide a differential porous PTFE structure composed of fibers and nodes connected to one another by these fibers. The microfibrous structure has a portion within the cross-section that possesses a different pore size, accompanied by a different node and fiber geometry, than adjacent areas within that cross section. In a vascular graft, the pores taper inwardly, providing a fluid-tight lumen wall structure that prevents leakage, yet promotes cellular ingrowth and natural tissue regeneration. A node structure of radially-oriented plates provides flexibility, suture strength, and enhanced protection against collapse.

27 Claims, 7 Drawing Sheets

U.S. PATENT DOCUMENTS

| | | | |
|---|---|---|---|
| 4,321,711 | 3/1982 | Mano | 3/1.4 |
| 4,332,035 | 6/1982 | Mano | 3/1.4 |
| 4,385,093 | 5/1982 | Hubis | 428/316.6 |
| 4,416,028 | 11/1983 | Eriksson et al. | 3/1.4 |
| 4,442,133 | 4/1984 | Greco et al. | 427/2 |
| 4,478,665 | 10/1984 | Hubis | 264/127 |
| 4,478,898 | 10/1984 | Kato | 264/127 |
| 4,482,516 | 11/1984 | Bowman et al. | 264/127 |
| 4,487,567 | 12/1984 | Possis et al. | 425/403 |
| 4,496,507 | 1/1985 | Okita et al. | 264/288.8 |
| 4,530,113 | 7/1985 | Matterson | 623/1 |
| 4,536,179 | 8/1985 | Anderson et al. | 604/266 |
| 4,550,447 | 11/1985 | Seiler, Jr. et al. | 623/1 |
| 4,563,485 | 1/1986 | Fox, Jr. et al. | 523/113 |
| 4,576,608 | 3/1986 | Homsy | 623/11 |
| 4,581,028 | 4/1986 | Fox, Jr. et al. | 623/2 |
| 4,588,407 | 6/1986 | Isono et al. | 623/11 |
| 4,596,837 | 6/1986 | Yamamoto et al. | 521/145 |
| 4,598,011 | 7/1986 | Bowman | 428/221 |
| 4,612,337 | 9/1986 | Fox, Jr. et al. | 523/113 |
| 4,619,641 | 10/1986 | Schanzer | 604/8 |
| 4,643,715 | 2/1987 | Isono et al. | 604/4 |
| 4,647,416 | 3/1987 | Seiler, Jr. et al. | 264/118 |
| 4,675,361 | 6/1987 | Ward, Jr. | 525/92 |
| 4,687,482 | 8/1987 | Hanson | 623/1 |
| 4,710,331 | 12/1987 | Nobuo et al. | 264/288.8 |
| 4,713,070 | 12/1987 | Mano | 623/1 |
| 4,743,252 | 5/1988 | Martin, Jr. et al. | 623/1 |
| 4,743,480 | 5/1988 | Campbell et al. | 428/36 |
| 4,749,585 | 6/1988 | Greco et al. | 427/2 |
| 4,760,102 | 7/1988 | Moriyama et al. | 521/145 |
| 4,795,459 | 1/1989 | Jauregui | 623/1 |
| 4,816,339 | 3/1989 | Tu et al. | 428/421 |
| 4,820,787 | 4/1989 | Kataoka et al. | 526/255 |
| 4,822,352 | 4/1989 | Joh et al. | 623/1 |
| 4,822,361 | 4/1989 | Okita et al. | 623/12 |
| 4,824,898 | 4/1989 | Sukigara et al. | 524/401 |
| 4,850,999 | 7/1989 | Planck | 623/1 |
| 4,859,535 | 8/1989 | Shinomura et al. | 428/398 |
| 4,863,442 | 9/1989 | DeMello et al. | 604/282 |
| 4,867,173 | 9/1989 | Leoni | 128/772 |
| 4,871,361 | 10/1989 | Kira | 623/1 |
| 4,876,332 | 10/1989 | Tsilibary et al. | 530/326 |
| 4,877,661 | 10/1989 | House et al. | 428/34.9 |
| 4,879,135 | 11/1989 | Greco et al. | 427/2 |
| 4,882,113 | 11/1989 | Tu et al. | 264/127 |
| 4,909,799 | 3/1990 | Thulesius et al. | 604/265 |
| 4,911,717 | 3/1990 | Gasill, III | 623/11 |
| 4,914,146 | 4/1990 | Honda et al. | 524/449 |
| 4,923,457 | 5/1990 | Ellingsen | 604/891.1 |
| 4,955,899 | 9/1990 | Della Corna et al. | 623/1 |
| 4,960,423 | 10/1990 | Smith | 623/1 |
| 4,973,609 | 11/1990 | Browne | 521/81 |
| 5,026,513 | 6/1991 | House et al. | 264/288.8 |
| 5,028,597 | 7/1991 | Kodama et al. | 514/56 |
| 5,064,593 | 11/1991 | Tamaru et al. | 264/113 |
| 5,071,609 | 12/1991 | Tu et al. | 264/289.3 |
| 5,071,610 | 12/1991 | Hagen et al. | 264/120 |
| 5,100,392 | 3/1992 | Orth et al. | 604/175 |
| 5,102,921 | 4/1992 | Harada et al. | 521/134 |
| 5,104,400 | 4/1992 | Berguer et al. | 264/132 |
| 5,104,402 | 4/1992 | Melbin | 623/1 |
| 5,104,403 | 4/1992 | Brotzu et al. | 623/1 |
| 5,110,527 | 5/1992 | Harada et al. | 264/127 |
| 5,217,666 | 6/1993 | Tamaru et al. | |

METHOD OF MAKING CONTROLLED POROSITY EXPANDED POLYTETRAFLUOROETHYLENE PRODUCTS

This application is a continuation-in-part of Ser. No. 850,862 filed by the inventors on Mar. 13, 1992.

BACKGROUND OF THE INVENTION

Many fluoropolymer materials, such as polytetrafluoroethylene (PTFE), are thermoplastic polymers. That is, they have the property of softening when heated and of hardening again when cooled. PTFE is generally produced in the form of white powder referred to as resin. It has a higher crystalline melting point (327° C.) and higher viscosity than other thermoplastic polymers, which makes it difficult to fabricate in the same manner as other plastics.

PTFE is a long chain polymer composed of $CF_2$ groups. The chain length determines molecular weight, while chain orientation dictates crystallinity. The molecular weight and crystallinity of a given resin prior to sintering are controlled by the polymerization process.

Currently, three different types of PTFE resins are available which are formed from two different polymerization processes. The three resins are granular polymer, aqueous dispersions, and coagulated dispersion products.

In the coagulated dispersion of PTFE resin, small diameter (0.1–0.2 micrometer) particles are coagulated under controlled conditions to yield agglomerates ranging in size from 400 to 500 micrometers in diameter. The morphological structure of these agglomerates can be considered as long chains of PTFE that are intermingled in a tangled network.

A known method of forming articles from fluoropolymer resins, such as PTFE, is to blend a resin with an organic lubricant and compress it under relatively low pressure into a preformed billet. Using a ram type extruder, the billet is then extruded through a die in a desired cross-section. Next, the lubricant is removed from the extruded billet by drying or other extraction method. The dried extruded material (extrudate), is then rapidly stretched and/or expanded at elevated temperatures. In the case of PTFE, this results in the material taking on a microstructure characterized by elongated nodes interconnected by fibrils. Typically, the nodes are oriented with their elongated axis perpendicular to the direction of stretch.

After stretching, the porous extrudate is sintered by heating it to a temperature above its crystalline melting point while it is maintained in its stretched condition. This can be considered as an amorphous locking process for permanently "locking-in" the microstructure in its expanded or stretchbed configuration.

It has been found that the effect caused by stretching PTFE is dependent on extrudate strength, stretch temperature, and stretch rate. According to U.S. Pat. No. 3,953,566 of W. L. Gore, products expanded at high rates of stretch have a more homogenous structure and possess much greater strength. Extrudate strength is more generally a function of the molecular weight and degree of crystallinity of the starting resin and extrusion conditions such as extrusion pressure, lubricant level, and reduction ratio. These parameters also control the degree of alignment that results from extrusion. The degree of alignment, in turn, affects one's ability to homogeneously stretch the extrudate.

Molecular weight and crystallinity affect the stretch characteristics, sinter profile and ultimately the final properties of the processed material. For the initial stages of fabrication, most PTFE fine powders used for ram extrusion and expansion processing are highly crystalline (>90%) as determined by IR spectroscopy, but their molecular weights may differ.

Low molecular weight materials tend to crystallize quickly and become highly crystalline and very brittle. In addition, the intermolecular forces between difluoromethylene groups are very low. Thus, in order to achieve adequate strength, one needs either very high molecular weight, highly crystalline material or one needs some way to disrupt the crystalline order. With a homopolymer, the best way to inhibit crystallization is to increase the viscosity of the molten material to very high values by selecting a polymer with very high molecular weight. In fact, PTFE coagulated dispersion resins that have very high molecular weights with molecular weight distributions have been developed for expanded PTFE processes.

In line with these considerations, the primary function of the "sintering" step is to heat the polymer above its crystalline melt point so that it can be reformed upon cooling to a low enough crystalline content to achieve the sort of mechanical properties required for the current application. To maintain a low crystalline content in the final product, the melt viscosity, corresponding to the molecular weight of the polymer, must be very high.

Most known methods for processing PTFE describe unilateral stretching techniques and stress the importance of stretching the fluoropolymer at rapid rates. For example, U.S. Pat. Nos. 3,953,566 and 4,187,390 issued to Gore state that while there is a maximum rate of expansion beyond which fracture of the material occurs, the minimum rate of expansion is of much more practical significance. Indeed, the patents state that at high temperatures within the preferred range for stretching (35° C.–327° C.) only the lower limit of expansion rate has been detected. The patents estimate this rate to be ten percent of the initial length of the starting material per second. The patents go on to note that the lower limit of expansion rates interact with temperature in a roughly logarithmic fashion so that at higher temperatures within the preferred stretching range, higher minimum expansion rates are required.

U.S. Pat. No. 4,973,609 to Browne describes another method for producing porous PTFE products by stretching at a rate of 10% per second. The patent also states that a differential structure is obtained by using an alloy of two different fluoropolymer resins which are characterized by significantly different stretch characteristics. The resins have different molecular weights and/or crystallinities. Accordingly, the final physical properties, such as strength, of PTFE articles formed in such a way are affected by the different molecular weights and/or crystallinities of the starting resins.

U.S. Pat. Nos. 4,208,745 and 4,713,070 also describe methods for producing porous PTFE products having a variable structure. The processes utilize a sintering step having a differential sintering profile. That is, one surface of an expanded PTFE article is sintered at a temperature which is higher than the sintering temperature of another surface. This results in fibrils being broken and provides an inherently weak material.

SUMMARY OF THE INVENTION

It is an object of the invention to provide a process for producing a shaped porous article which is more truly semi-permeable than known articles formed of fluoropolymer materials. It is another object of the invention to provide such a process in which a fluoropolymer extrudate can be homogeneously stretched independently of rate. Still another object is to provide a porous article. Yet another object of the invention is to provide a porous article; having a porosity which is variable in the direction of the article's cross-section.

These and other objects are achieved by the present invention which in one aspect features a process for producing a porous article. The process includes the steps of providing an extrudate of a fluoropolymer material which is capable of being stretched and bilaterally stretching the extrudate along its longitudinal axis. Conditions are maintained during stretching sufficient to yield an article which is substantially uniformly stretched over a major portion of its length. These conditions include stretch rate, ratio, and temperature.

The stretched extrudate has a microstructure which is characterized by elongate nodes which are connected by fibrils. This microstructure is locked in by sintering the stretched extrudate while maintaining it in its stretched state.

An important feature of the invention is that the fluoropolymer extrudate is bilaterally stretched. That is, in accordance with the invention both ends of the extrudate are displaced along the extrudate's longitudinal axis away from a central portion of the extrudate. It has been found that this stretching method provides significant advantages over known stretching methods wherein one end of an extrudate is held stationary while only the other end is displaced.

In various embodiments of this aspect of the invention the bilateral stretching is carried out at rates not greater than ten percent per second. Indeed, it has been found that stretching at rates slower than even one percent per second provides a material having an extremely desirable microstructure of nodes and fibrils, the nodes being significantly larger than nodes resulting from known processes of rapidly stretching single-resin extrudates unilaterally.

In carrying out the stretching step in accordance with the process of the invention, the ends of the extrudate can be displaced either simultaneously or sequentially. For example, in one embodiment of the invention, a first end of the extrudate is displaced to a stretch ratio of not greater than two to one. That first end is then held stationary while the second end of the extrudate is displaced in the opposite direction to again result in a stretch ratio of not greater than two to one. Restricting the individual stretches to stretch ratios of not greater than two to one ensures a substantially homogeneous microstructure along a major portion of the length of the extrudate.

In another aspect, the invention features a process for producing a porous tube of polytetrafluoroethylene including the step of providing a preformed billet of a mixture of a polytetrafluoroethylene resin and a lubricant. As with the above-described aspect of the invention, the billet is extruded, the extrudate is then dried, and bilaterally stretched along its longitudinal axis under conditions sufficient to yield a tube having a substantially homogenous microstructure over a major portion of its length. The stretched tube is then sintered while being maintained in its stretched state to produce the porous tube.

In one embodiment of this aspect of the invention, the preformed billet is formed to have a lubricant level which selectively varies in the direction of the billet's cross-section. That is, for example, the billet might have a lubricant level of fifteen percent by weight at its inner and outer surfaces and a lubricant level of approximately twenty percent at a radial position between its inner and outer surfaces. When extruded and stretched, such a billet results in a porous tube having a microstructure which varies in a controlled fashion in the direction of the tube's cross-section. This phenomenon and its advantages are described below in greater detail.

Accordingly, in the various embodiments of this aspect of the invention, a porous article having a desired microstructure is provided by controlling the billet lubricant level, the billet reduction ratio, and bilateral stretching conditions such as stretch rate and ratio. These steps avoid the problems such as weak material which are associated with known resin-blending and varied-profile sintering techniques.

In still another aspect, the invention features a tube formed of an expanded porous fluoropolymer material. The material has a microstructure characterized by ring shaped nodes interconnected by fibrils. An important feature of this aspect of the invention is that substantially all of the nodes each circumscribes, at least in part, the longitudinal axis of the tube and extends from the inner to the outer surface of the tube wall, thereby creating between the nodes continuous through-pores from one surface to the opposite surface.

In accordance with yet another aspect, the invention features a tube formed of porous fluoropolymer material characterized by a structure of nodes and fibrils wherein the nodes are radially oriented and the fibrils extend substantially parallel to the axis of the tube between successive nodes, the nodes and fibrils forming pores having radially tapering size distribution conducive to tissue through-growth.

These and other features of the invention will be more fully appreciated by reference to the following detailed description which is to be read in conjunction with the attached drawings.

DETAILED DESCRIPTION

Figure 1:
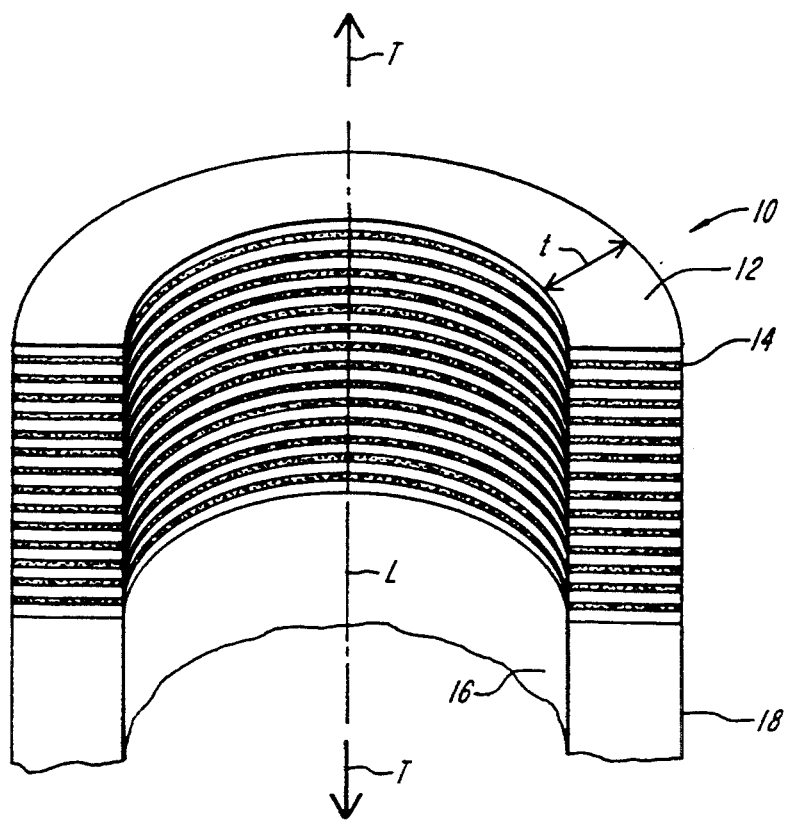
FIG. 1 is a schematic representation of a porous article formed in accordance with the teachings of the present invention.

As stated above, in one aspect the invention features a process for producing a shaped porous article. A significant feature of the process is that an article having a homogeneous microstructure is formed independently of the rate at which it is stretched.

By homogenous microstructure, in this patent application, it is intended to convey first that the microstructure of the article, including relatively dense nodes separated by relatively light connecting fibrils, is relatively uniform along at least one dimension, e.g., the length of the article, although as will be explained below, aspects of microstructure may be, and preferably are, intentionally varied in another direction, e.g., in cross-section of the article.

Various fluoropolymer resins are suitable for use in the present invention. For example, polytetrafluoroethylene or copolymers of tetrafluoroethylene with other monomers may be used. Such monomers may be ethylene, chlorotrifluoroethylene, perfluoroalkoxytetrafluoroethylene, or fluorinated propylenes such as hexafluoropropylene. In particular, however, polytetrafluoroethylene (PTFE) works well. Accordingly, while the inventive process can be utilized to produce porous articles formed of various fluoropolymer materials, the following description pertains specifically to the formation of an article from PTFE resin.

For purposes of the present invention, all fluoropolymers that require a lubricant/extrusion aid and are capable of being expanded can be used. However, it is preferred to use highly crystalline, high molecular weight resins to achieve maximum strength. When PTFE is used, resin of a molecular weight between 5,000,000 and 70,000,000 is suitable.

It should be noted, however, PTFE does not dissolve in any common solvent; therefore its molecular weight cannot be measured by the usual methods. According to the *Encyclopedia of Polymer Science and Engineering* (Wiley and Sons, 1989), though, the following relationship has been established between number-average molecular weight (Mn), for molecular weights between $5.2 \times 10^5$ and $4.5 \times 10^7$, and the heat of crystallization ($\Delta Hc$) in Joules/gram (calories/gram).

$$Mn = (2.1 \times 10^{10}) \times \Delta Hc^{-5.16}$$

Accordingly, by determining the heat of crystallization of a given PTFE resin, a number average molecular weight of the resin is determined using this relationship.

As with known methods of processing PTFE, the invention utilizes a preformed billet which comprises a PTFE resin mixed with an organic lubricant. Various lubricants are suitable such as naphtha, ISOPAR-G and ISOPAR-H available from Exxon Corporation. Low odor paraffin solvents can be used as well. The blended resin is compressed at low pressure (less than 1000 PSI) into a tubular billet of approximately one third of the resin's original volume. Billet forming processes are generally known in the art.

As discussed above, extrusion conditions have a significant effect on the resulting extrudate's reaction to being stretched. In particular, once a resin of a given molecular weight and crystallinity has been selected, extrudate qualities are controlled by the level of lubricant mixed with the resin to form the billet, the reduction ratio at which the billet is extruded and the extrusion pressure. These are believed to influence the micromechanical properties of the extruded article because these parameters affect the degree to which the molecular chains of PTFE align themselves during extrusion.

The process of the invention is most effective when using preformed billets ranging in lubricant level from between 8 to 25 percent by weight to produce an extrudate well adapted for the inventive stretching process.

When PTFE extrudate is subjected to an external tensile force, such as during stretching, the intermingled network of PTFE particles separate. Accordingly, the force required to separate these particles, and hence stretch the extrudate, is dependent upon the degree of intermingling of the PTFE particles. The longer the polymer chains (higher molecular weight), the greater the amount of intermingling that will occur and, therefore, the greater the force that will be required to separate the coagulated dispersion particles.

Two other extrusion parameters having an effect on a resulting extrudate's reaction to stretching are reduction ratio and extrusion pressure. The range of suitable reduction ratios is bounded at its lower end by the minimum reduction ratio permissible which provides an extrudate of sufficient strength so as not break during stretching. At its upper limit, the range of suitable reduction ratios is bounded by the maximum ratio permissible which provides an extrudate that is amenable to being homogeneously stretched. Accordingly, experimentation has shown that for purposes of the present invention the preformed billet should be extruded to a reduction ratio of between approximately 50:1 and 600:1. A preferred reduction ratio is between approximately 200:1 and 400:1.

Reduction ratio and stretch characteristics are interrelated since the force required to deform a PTFE extrudate and form fibrils from the nodes is related to how the material was aligned (packing density) during extrusion. Fibrils are not formed as easily from nodes with high reduction ratio extrudates as they are with low reduction ratio extrudates. This is believed to be because internal forces are much higher in high reduction ratio extrudates.

The third extrusion parameter which has a significant effect on the resulting extrudate's properties upon being stretched is extrusion pressure. While extrusion pressure is, to a certain extent, related to reduction ratio, by varying lubricant level, extrusion pressure can be varied independently of reduction ratio. While measured extrusion pressure will vary depending upon the type of extrusion equipment being used, the range of suitable extrusion pressures to practice the present invention will be apparent to those skilled in the art. For example, pressures between approximately 6000 PSI and approximately 10,000 PSI have been used successfully for the practice of the invention.

Once an extrudate has been produced according to the above described parameters, in accordance with the inventive process it is stretched under conditions sufficient to yield an article that is uniform over a major portion of its length. Stretching processes are characterized in terms of stretch rate and stretch ratio. Stretch rate refers to the percentage change in length of the extrudate per unit time. In the case of a fifty centimeter long extruded tube, for example, stretching five centimeters per second results in a stretch rate of ten percent per second. The percentage change is calculated with reference to the initial length of the extrudate.

Stretch ratio, on the other hand, is not time dependent but merely refers to the ratio of the final length of the stretched extrudate to that of the initial length of the unstretched extrudate. Accordingly, stretching a fifty centimeter long extruded tube to one hundred centimeters, results in a stretch ratio of 2:1 regardless of the duration of the stretch.

With this in mind, it is an important feature of the invention that extruded materials are stretched to form porous articles independently of stretch rate. In certain instances the process is dependent on stretch ratio. As stated above, known methods for processing fluoropolymer materials teach that stretching must be carried out at a rate generally exceeding approximately ten percent per second. In accordance with the invention, however, homogeneous articles are produced at stretch rates not greater than approximately ten percent per second. Indeed, the preferred rate of stretching ranges from approximately 0.5 percent per second to approximately 10 percent per second.

TO stretch an extrudate, the extrudate must be placed in tension. This is done by applying opposed forces to the ends of the extrudate. The level of force applied to the extrudate, and hence the rate at which the extrudate stretches, determines how the above-described intermingled network of PTFE particles unravels. In known methods for stretching PTFE, force is applied to place the extrudate in tension by displacing one end of the extrudate with respect to the other end. At stretch rates lower than ten percent per second, this method of stretching cannot uniformly stretch the extrudate to greater than a 2:1 ratio. To the contrary, at greater ratios the material stretches preferentially at its moving end. The fixed end of the material, on the other hand, experiences significantly less stretching.

In accordance with the invention, on the other hand, bilateral stretching results in more even force distribution along the length of the extrudate and produces a more homogeneously stretched material. It has been found that stretching bilaterally, that is, displacing both ends of the extrudate away from the middle of the extrudate, provides a material that is homogeneously stretched over the majority of its length independent of the stretch rate.

After the extrudate has been bilaterally stretched it is sintered by heating it above its crystalline melting point under tension. As discussed above, this locks in the microstructure of the material and completes the process of producing the porous article.

FIG. 1 is a schematic representation of a porous tube 10 formed by the above described bilateral stretching process. For purposes of description, the microstructure of the tube 10 has been exaggerated. Accordingly, while the dimensions of the microstructure are enlarged, the general character of the illustrated microstructure is representative of that microstructure prevailing in an article formed by the inventive process.

The tube 10 includes a microstructure characterized by elongate nodes 12 interconnected by fibrils 14. A significant feature of the tube 10 is that the nodes 12 are ring-shaped to form, in effect, a series of washer-type, or plate-like solid bodies circumscribing the tube's longitudinal axis L. The nodes 12 are oriented generally radially, i.e., perpendicularly to the axis of stretching, represented by arrows T which is coincident with the longitudinal axis L.

Another significant feature of the tube's microstructure is that substantially all of the nodes 12 extend along a transverse axis t from an inner surface 16 of the tube to an outer surface 18 of the tube. This dimension of the nodes 12 along the inside-to-outside direction is significantly larger than the corresponding dimension of nodes formed by conventional single-resin fluoropolymer processing methods. Such nodes are randomly arranged and may be characterized by a transverse axis which is generally oriented perpendicularly to the axis of stretch. Notably, however, the nodes of these known structures are considerably shorter and smaller than nodes produced in accordance with the present invention. Indeed, the above-referenced U.S. patents to Gore note that nodes formed by that known technique generally range in size from smaller than one micron to approximately 400 microns.

Unlike the short, randomly stacked nodes and microfibrillar spaces formed by conventional single-resin fluoropolymer stretch or expansion processing, the method of the present invention provides a microporous structure having microfibrillar spaces which define through-pores or channels extending entirely from the inner to the outer wall of the expanded extrudate. These through-pores are perpendicularly oriented internodal spaces which traverse from one surface to another.

As discussed below in greater detail, by varying lubricant levels such internodal through-pores are preferentially altered in accordance with the present invention such that the surface pore on one surface is made to be larger or smaller than the surface pore on the opposing surface.

Figure 2:
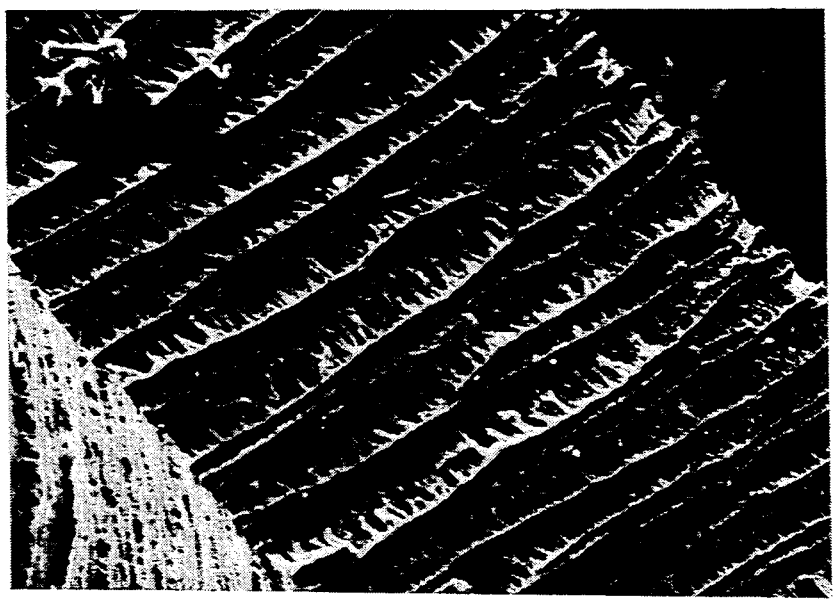
FIG. 2 is a scanning electron microscopic view of a longitudinal cross-section of a porous article in accordance with the invention.

A longitudinal cross-section view of a tubular article formed by the process of the invention is shown in FIG. 2. There, it can be seen that the present invention produces an article having a microstructure characterized by elongate nodes which are substantially larger than the nodes of materials produced by known single-resin forming methods. Indeed, the nodes shown in FIG. 2 consistently range in size from approximately 500 microns to approximately 900 microns. Substantially all of the nodes of the article shown in FIG. 2 extend from the inner surface of the tubular article to the outer surface of the tubular article, thereby creating through-pores substantially all of which traverse from one surface of the article to the other.

Figure 3:
FIG. 3 is a scanning electron microscopic view of a radial cross-section of a porous article in accordance with the invention.

FIG. 3 is a radial cross-section view of the tubular article shown in FIG. 2. There it can be seen that while the nodes are generally oriented perpendicularly to the axis of stretch, as represented in FIG. 1, they are not perfectly flat and, therefore, a radial cross-section cuts through many nodes. Accordingly, while the schematic representation in FIG. 1 is useful for purposes of explanation, the scanning electron microscope photographs in FIGS. 2 and 3 are more accurate depictions of the microstructure of a product produced by the inventive process.

Products provided by the invention are suitable for a wide range of biological applications such as for vessel implants or organ wall grafts. In particular, as described below, vascular grafts formed by the process of the invention enjoy various advantages. Indeed, the processes of the invention are well suited for the formation of the various biological devices described in the following commonly assigned and co-pending United States Patent Applications: U.S. Ser. No. 760,753 for "IMPLANTABLE PROSTHETIC DEVICE FOR THE DELIVERY OF A BIOACTIVE MATERIAL"; U.S. Ser. No. 760,716 for "MANUALLY SEPARABLE MULTI-LUMEN VASCULAR GRAFT"; U.S. Ser. No. 760,728 for "IMPLANTABLE PROSTHETIC DEVICE HAVING INTEGRAL PATENCY DIAGNOSTIC INDICIA"; U.S. Ser. No. 760,717 for "POLYLUMENAL IMPLANTABLE ORGAN"; and U.S. Ser. No. 760,718 for "SELF-SEALING IMPLANTABLE VASCULAR GRAFT" all of which were filed 16 Sep. 1991. The specifications of these applications for patent are hereby incorporated herein by reference.

As stated, several structural, clinical and biological advantages accrue from the microstructure engendered by the inventive process. For example, as discussed below in greater detail with regard to the various examples, larger node size provides a structure having a significantly improved radial tensile strength. Also, tubes formed by the inventive process have improved burst pressure and suture strength characteristics. The flat ring-like node structure imparts significantly more flexibility, without kinking, than conventional fluoropolymer processes, in addition to providing superior resistance to radial twist compression (colloquially known as "torque twist"). The tubular article formed by the process of the invention allows a significant degree of bending or radial twist, before experiencing lumen collapse or kinking, unlike conventional fluoropolymer articles which exhibit significantly less resistance to "torque twist" or "bending." Conventional articles, therefore, kink under smaller stress loads than do the articles of the current invention.

Additionally, the method of the current invention produces articles which exhibit significantly more resistant to compression than conventionally processed articles. This provides more resistance to luminal collapse under equivalent stress loads. The articles provided by the invention also exhibit increased flexibility for enhanced drapability, or ability to bend more readily, without restricting luminal cross-sectional area, thereby improving ease of handling during surgery, while not increasing stress on the points of attachment and fixation. The ring like nodal architecture of the invention also produces tubular structures with significantly more resistance to tearing or splitting in the horizontal direction, as compared to conventional non-reinforced fluoropolymer tubular articles.

For experimentation, an extrudate was prepared by blending PTFE resin (Fluon CD-123 obtained from ICI Americas) with "ISOPAR-H" odorless solvent (produced by Exxon Corporation) used as an extrusion aid at a level of 150 cc of solvent per pound of resin. The blend was compressed into a tubular billet, heated to 300° C., and extruded into a 6 mm I.D. by 7 mm O.D. tube in a ram extruder having a reduction ratio of about 149:1 in cross-sectional area from billet to the extruded tube. The volatile extrusion aid was removed by drying in a heated oven prior to stretching.

To demonstrate the advantages of bilateral stretching in accordance with the invention, samples of the tubular extrudate were then stretched various ways as discussed below.

METHOD 1

An apparatus was developed that allowed samples of the tubular extrudate to be stretched at controlled rates and temperatures. The apparatus consisted of two clamps for holding the tube, one clamp held fixed within the oven and another clamp attached to a chain drive coupled to a variable speed motor. The tube was stretched an amount equal to 50% of its original length at a rate of approximately 10% per second. The fixed and moveable ends were then inverted and the stretching step repeated. The stretch and inversion steps were repeated until the extrudate sample had been stretched to a final stretch ratio of three to one. The oven temperature was then raised to 370° C. for ten minutes while the samples were held clamped.

METHOD 2

An apparatus was developed that allowed both ends of the extrudate to be displaced simultaneously, at a controlled temperature and rate. The apparatus included two clamps independently mounted to two slide drive systems. Following mounting to the stretch apparatus, both sides of the sample were displaced simultaneously at equal speeds in opposite directions for a selected distance. The applied stretch rate-using the combined displacements rates from each side was calculated to be approximately 10% per second. The final stretch ratio was approximately three to one.

METHOD 3

The apparatus described in Method 2 was used to displace each end of the extrudate sequentially. That is, first one end of the extrudate was held fixed while the other was displaced a given distance at a constant speed, then, without inverting the sample, the previously displaced end was held stationary while the formerly stationary end was displaced the same distance at the same speed. Again, the sample was stretched at a rate of approximately 10% per second to a final ratio of approximately three to one.

Samples produced by the above described methods were then tested along with commercially available PTFE tubes produced by conventional, unilateral stretch techniques, the results appearing below.

| SAMPLE | A | B | C | D | E | F |
|---|---|---|---|---|---|---|
| Conventional | 3969 | 640 | 7.9 | 55 | 2.2 | 800 |
| Method 1 | 2660 | 803 | 2.9 | 90 | 0.5 | 1462 |
| Method 2 | 2720 | 833 | 2.8 | 95 | 0.5 | 1382 |
| Method 3 | 2400 | 845 | 2.8 | 95 | 0.5 | 1861 |

Where A is longitudinal tensile strength (pounds per square inch);

where B is radial tensile strength (pounds per square inch);

where C is water entry level (pounds per square inch);

where D is radial burst pressure (pounds per square inch);

where E is ethanol bubble point (pounds per square inch); and where F is suture strength (in grams) for a 2 mm bite.

Further, tubular extrudate samples as produced above were bilaterally stretched, displacing both ends simultaneously, at other stretch rates. Again, the stretch rates were calculated by combining the displacement rates of both ends of the extrudate. Tests performed on samples produced in this manner yielded the results detailed below.

|  | A | B | C | D | F |
|---|---|---|---|---|---|
| 10%/sec | 2232 | 780 | 2.8 | 95 | 1838 |
| 5%/sec | 2144 | 933 | 2.4 | 90 | 1657 |
| 0.5%/sec | 2372 | 953 | 2.1 | 105 | 1612 |

The data clearly indicate that enhanced radial strength and suture strength along with a corresponding decrease in Water Entry Pressure and Ethanol Bubble Point, result from the inventive bilateral stretching process.

For purposes of evaluating homogeneity, additional tubular extrudate samples were marked at ½" spaced intervals using a permanent marker. The samples were mounted and stretched either unilaterally with one end held fixed throughout the stretching process or bilaterally in which both ends were displaced simultaneously. After stretching at rates equal to or lower than 10% per second the samples were sintered and analyzed by measuring the distance between the marks along the sample lengths. This distance, divided by the original half-inch spacing yields a local measure of the expansion ratio. The results detailed below indicate that at low rates of stretch bilateral stretching produces a structure which is more uniform than unilaterally stretched products. That is, with the bilaterally stretched samples, each half inch segment stretched an amount comparable to all segments through the length of the sample. Each unilaterally stretched sample, on the other hand, stretched preferentially at its moving end, often by a factor three to five times greater than that of its restrained end.

| BILATERAL STRETCHING FINAL STRETCH LENGTH IN INCHES OF EACH SEGMENT | | | | |
|---|---|---|---|---|
| ORIGINAL DISTANCE FROM MIDDLE (INCHES) | 10%/SEC | | 5%/SEC | |
| | 3:1 RATIO | 4:1 RATIO | 3:1 RATIO | 4:1 RATIO |
| 2.0 | 1.375 | 1.75 | 1.25 | 1.75 |
| 1.5 | 1.375 | 1.875 | 1.5 | 2.0 |
| 1.0 | 1.375 | 1.875 | 1.375 | 2.0 |
| 0.5 | 1.5 | 1.875 | 1.5 | 1.875 |
| 0.5 | 1.5 | 1.75 | 1.5 | 1.875 |
| 1.0 | 1.5 | 2.0 | 1.5 | 2.0 |
| 1.5 | 1.5 | 2.0 | 1.375 | 1.875 |
| 2.0 | 1.5 | 1.75 | 1.5 | 2.0 |

It can be seen that at a rate of 10% per second, bilaterally stretching an extrudate to a ratio of 3:1 in accordance with the invention yields an achieved expansion factor that varies by under 10% along the length of the stretched extrudate. Bilaterally stretching to a 4:1 ratio at this rate yields a variation of less than 8%.

Bilaterally stretching at 5% per second yields similar uniformities in achieved expansion factor. Moreover, such variations as there are, appear to be distributed in a more spatially uniform way.

| UNILATERAL STRETCHING FINAL STRETCH LENGTH IN INCHES OF EACH SEGMENT | | | | | | |
|---|---|---|---|---|---|---|
| ORIGINAL DISTANCE FROM FIXED END (INCHES) | 10%/SEC | | 5%/SEC | | 0.5%/SEC | |
| | 3:1 RATIO | 4:1 RATIO | 3:1 RATIO | 4:1 RATIO | 3:1 RATIO | 4:1 RATIO |
| 0.5 | 1.25 | 1.375 | 1.0 | 0.5 | 0.875 | 0.75 |
| 1.0 | 1.125 | 1.5 | 1.0 | 0.5 | 0.875 | 0.75 |
| 1.5 | 1.0 | 1.75 | 1.0 | 0.875 | 0.875 | 0.75 |
| 2.0 | 1.125 | 1.875 | 1.125 | 1.5 | 1.0 | 1.0 |
| 2.5 | 1.375 | 2.25 | 1.25 | 1.875 | 1.375 | 1.75 |
| 3.0 | 1.625 | 2.375 | 1.5 | 3.5 | 1.875 | 3.5 |
| 3.5 | 2.125 | 2.75 | 2.125 | 4.0 | 2.25 | 4.0 |
| 4.0 | 2.875 | 2.75 | 2.375 | 4.0 | 2.625 | 4.25 |

These results show that with unilateral stretching at the above-noted rates and ratios, a far greater variation in achieved expansion results. In particular, the results show that at these rates and ratios, a unilaterally stretched sample stretches preferentially at its moving end.

Figure 4:
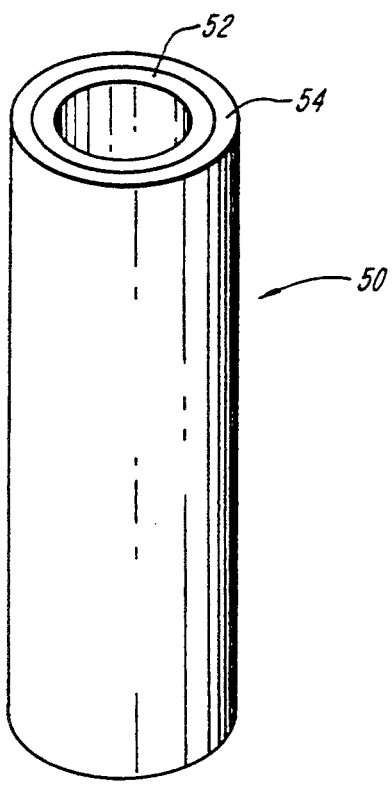
FIG. 4 is a schematic depiction of a billet suitable for extrusion in accordance with the invention.

In another embodiment of the invention, a porous article is formed utilizing a preformed billet such as billet 50 shown in FIG. 4. Billet 50 includes radial inner portion 52 and radial outer portion 54. A significant feature of billet 50 is that while radial portions 52 and 54 comprise the same resin, different lubricant properties prevail in the portions. For example, different types of lubricant, different molecular weight lubricants of the same type, lubricants of different viscosity, or a single lubricant but at different relative proportions may be used.

The formation of layered preform billets is generally known in the art. For example, various known techniques have been used to produce extrudates having a conductive layer in electronic applications or a colored layer in general tubing applications. U.S. Pat. No. 4,973,609 assigned to Browne describes a layering technique using different resins.

In accordance with this aspect of the present invention, the microstructure of an extruded and expanded PTFE article is controlled using a single resin with a varying lube characteristic, preferably the lube level, through the preform billet. For instance, the sample shown in FIGS. 5A through 5C was produced using a single PTFE resin that was preformed in a layered fashion at two different lube levels across its cross-section and processed according to the above described bilateral stretching process.

Figure 5A:
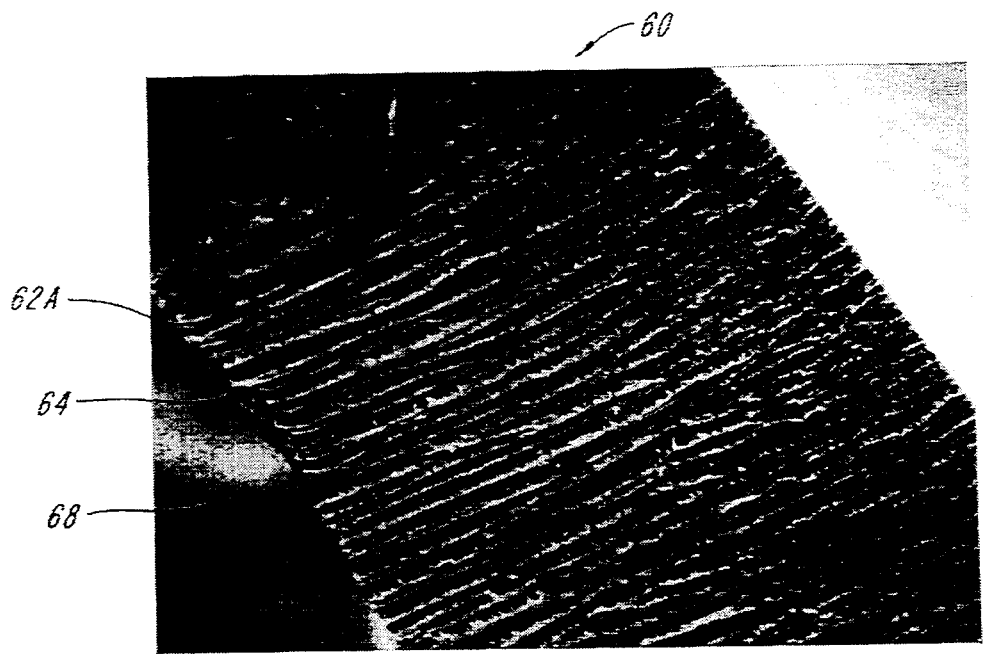
FIG. 5A is a scanning electron microscope longitudinal cross-section view of another porous article in accordance with the invention.
Figure 5B:
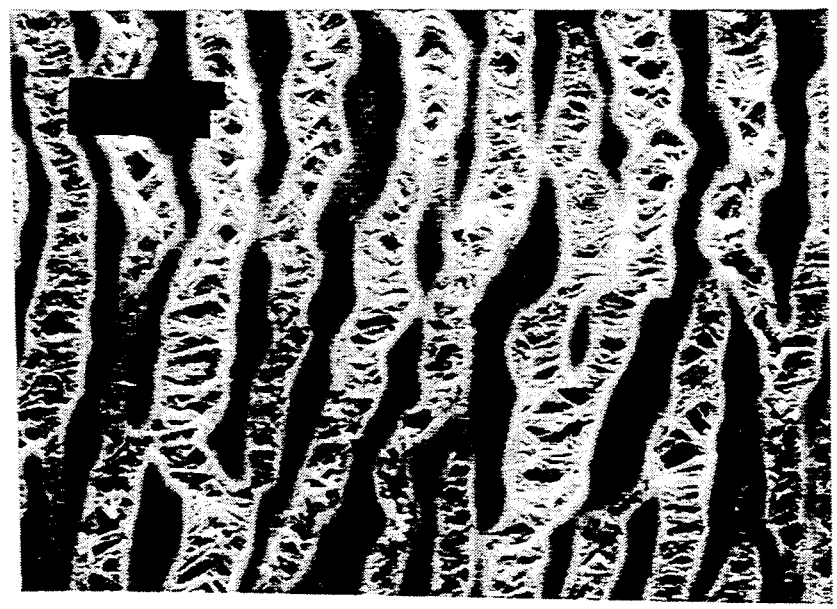
FIG. 5B is a scanning electron microscope view of the inner surface of the porous article shown in FIG. 5A.
Figure 5C:
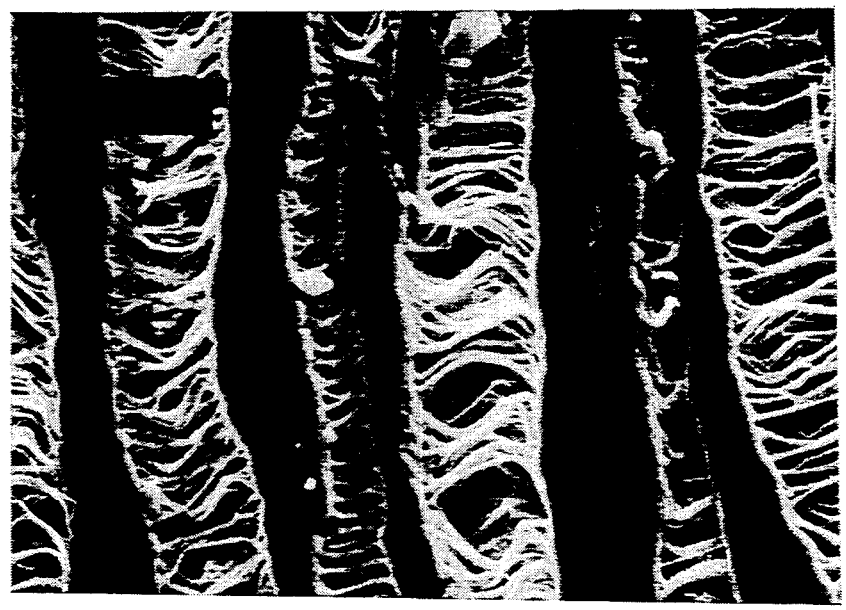
FIG. 5C is a scanning electron microscope view of the outer surface of the porous article shown in FIG. 5A.

FIG. 5A is a longitudinal cross-section view of a wall 60 of a tubular article formed utilizing the billet 50 in accordance with the above-described inventive process. As can be seen in the Figure, the material forming the wall 60 is characterized by a microstructure of large nodes 62A and small nodes 62B interconnected by fibrils 64. This results due to the inner radial portion 52 of billet 50 having a lower lubricant level than the outer radial portion 54. That is, lower lubricant levels result in smaller, more closely spaced nodes.

Several advantages accrue from the structure of wall 60. For example, by forming a tube having porosity at an inner surface 66 (FIG. 5B) which is smaller than the porosity at an outer surface 68 (FIG. 5C), a vascular graft is provided which defines an efficient flow channel at its inner surface while fostering improved cellular ingrowth at its outer surface.

Figure 6:
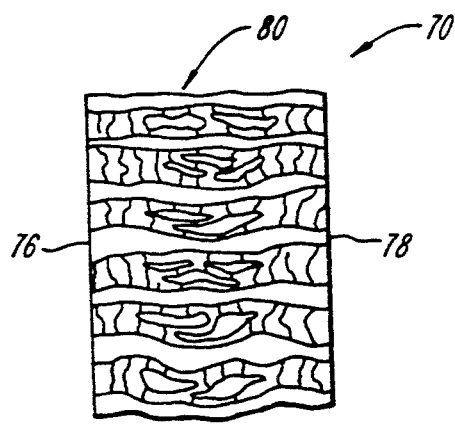
FIG. 6 is a schematic longitudinal cross-section view of still another porous article in accordance with the invention.

It should be understood that in addition to the illustrated embodiment, billets can be formed in accordance with the present invention having lubricant properties which vary in a selected pattern through the cross-section to achieve desired pore or channel distribution. For example, by forming a tubular billet which has a lubricant level which is different at a radial position of the cross-section from the lubricant level at another position, e.g., the inner or outer surfaces of the cross-section, and by carefully extruding a preform from the billet, a unique product is formed. For example, a tubular article having a wall 70, such as shown in FIG. 6, can be formed by this method. Note that the wall 70 has relatively large pores at its inner and outer surfaces 76 and 78 but includes a barrier region 80 of smaller pores between the inner and outer surfaces. Such a structure used as an implant or vascular graft is expected to promote cellular ingrowth from both sides of the wall 70 while preventing cellular growth completely through the wall.

From the fact that stretching of the extrudate yields an article with pore structure corresponding to the lube distribution of the preform, it appears that flow in the long tapered extrusion head is highly laminar. Such flow can result in a uniformity of PTFE molecular orientation. Applicant expects this property to result in an extrudate that, after sintering (but even without any stretching), will have high tensile strength, as compared to conventionally extruded materials. Accordingly, it is also comprehended within the scope of the present invention to extrude an extrudate from a billet of varying lube level or other characteristic, and, without stretching the extrudate, sinter it to fix its dimensions.

For biological applications, the unique through-pore orientation created by the individual nodal spaces is exploited, for example, to either increase or decrease the migration of certain cellular and or biological materials directly into or onto the inventive tubular structure. This results in improved biocompatibility. For example, it is well documented that specific cell types penetrate, grow into, or onto porous fluoropolymer structures. By providing a matrix of large, oriented nodes to present non-tortuous pathways, full cellular penetration is possible, without "dead ended" channels. This offers a significantly improved cellular environment, for example, to promote the growth of morphologically complete capillaries. The provision of large-entry channels with a taper offers similar advantages, with the added feature of precisely limiting the depth of tissue penetration. Hence the hybrid nodal structure design of this invention offers many structural, physical and biological characteristics not found with other, well documented pure fluoropolymer, composite or coated tubular articles.

In accordance with the invention, therefore, methods and materials are provided for the formation of biological implants having enhanced structures and tissue support features. Both organ wall grafts and vessel implants can be formed by practice of the invention. Representative methods of fabricating tube structures with taper nodal geometry will now be briefly described.

METHOD 4

PTFE resin identified as Fluon CD-123 obtained from ICI Americas was blended in two separate containers with 98 cc and 150 cc, respectively, per pound of resin, of an odorless mineral solvent, identified as Isopar-H produced by Exxon Corporation. The solvent serves as a lubricant for extrusion of the resin, in a manner well known in the art. The two resin/lube mixes were then separately poured into a preforming cylinder in concentric layers to form a billet or preform 50 as shown in FIG. 4. Inner layer 52 of extrusion preform 50 contained the lower lube level (98 cc lube/lb) resin. Outer layer 54 of preform 50 contained the higher lube level (150 cc/lb) resin. A core-rod cylinder was fitted over the core rod of the preforming cylinder to separate the layers during pouring. The cylinder was removed after pouring was completed, and the extrusion preform, or billet, was formed by compacting the layered mass under a compaction pressure of 600 psi, to produce a dense preform billet having a concentric stepped concentration of lube level.

The preform billet was then inserted into a ram extruder and extruded into a 4 mm I.D./5.3 mm O.D.tube, the ram extruder having a reduction ratio of 350:1 in cross-sectional area from preform to extruded tube. Fifteen inch samples were cut from the tubular extrudate and allowed to bake at 300° C. for five minutes prior to stretching in order to remove the lubricant, which was a volatile extrusion aid. The samples were then stretched at 300° C. at a rate of 0.5% per second to a length of 45 inches. Sintering was effected by clamping the tube ends and heating the restrained samples to a temperature of 370° C. for four minutes.

Figure 7A:
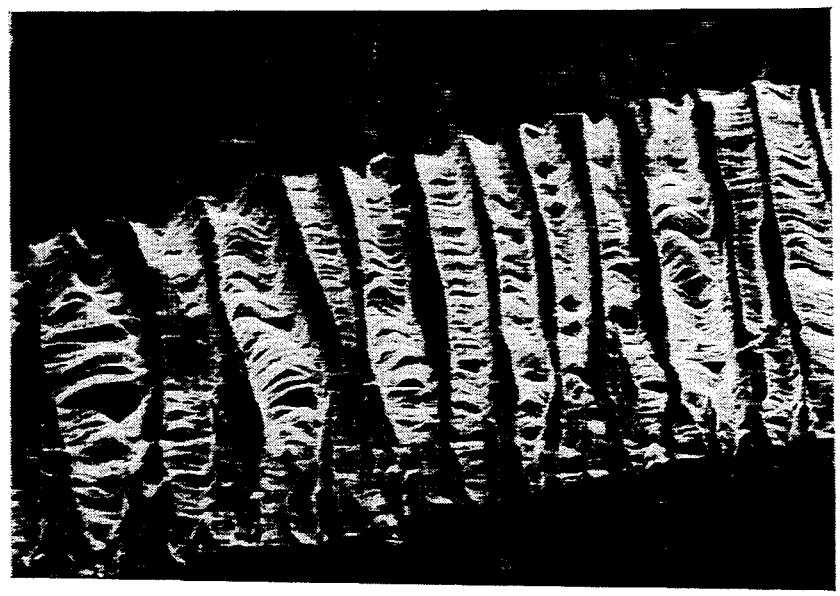
FIG. 7A is a photomicrograph of a radial section through the structure of FIG. 7.
Figure 7:
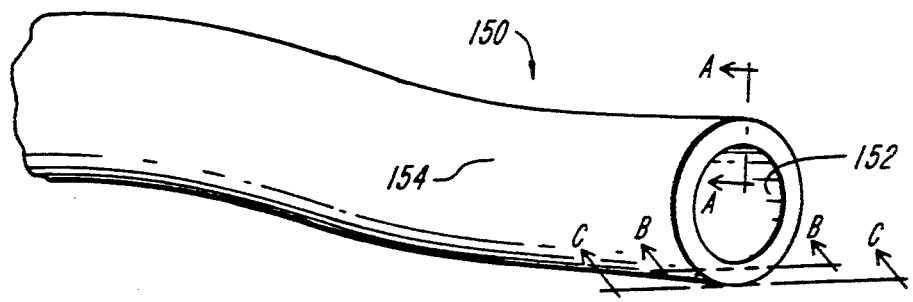
FIG. 7 is a schematic representation of a tubular structure according to a presently preferred embodiment of the invention.

FIG. 7 indicates in schema a tube structure 150 formed in this fashion having interior surface 152 and exterior surface 154, with the section lines A, B, and C identifying radial and inside and outside sections for which electron micrographs of a prototype tube are discussed below.

Figure 7B:
FIG. 7B is a photomicrography of a tangent section taken at the interior of the structure of FIG. 7.
Figure 7C:
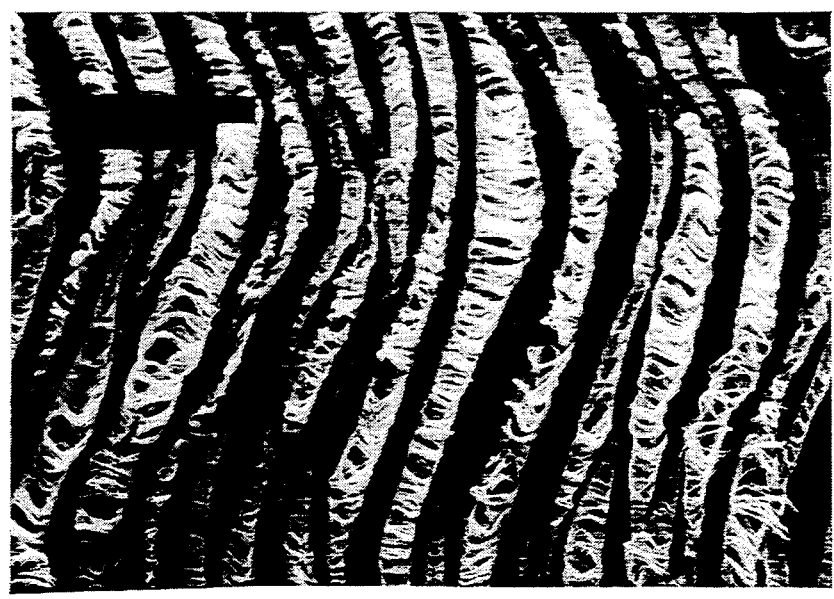
FIG. 7C is a photomicrograph of a tangent section taken of the exterior of the structure of FIG. 7, FIG. 8A schematically illustrates a tube preform with layered material of radially decreasing lube level.

Indicated sample sections of the expanded tube were then prepared and subjected to electron micrography as shown in FIGS. 7A–7C.

As best seen in the radial section, FIG. 7A, the inner surface 152 of a tube prepared in this manner has a more frequent node structure than the outer surface, with nodes spaced almost twice as frequently along the tube axis as at the outer surface 154. Fibril length is therefore necessarily shorter, but both inner and outer regions have full, densely-arrayed fibrils with none of the coalescence that characterizes the differential-heating approach to node tailoring of the prior art. Moreover, the diameter of the fibrils is essentially the same at the inside and outside regions.

As seen in FIG. 7C, the node-fibril structure in the radially outer portion of the tube is characterized by large intact node bodies, spaced 40-80 micrometers apart, whereas that of the radially inner portion has a node spacing in the range of 25-50 micrometers (FIG. 7B). The overall form of the nodes is that of flat plates oriented perpendicular to the tube axis, and extending in partial or complete annuli about the central lumen of the tube. The inside edges of the nodes may be seen to be somewhat fragmented or frayed in appearance, while still preserving the overall plate-like form and radial orientation of the outer portion, despite their closer spacing.

The resulting structure therefore has through-pores extending substantially continuously from the inside to the outside. In addition, applicant has found this material to have a strength comparable to conventional stretched PTFE products fabricated using much higher stretch rates.

METHOD 5

Figure 8A:
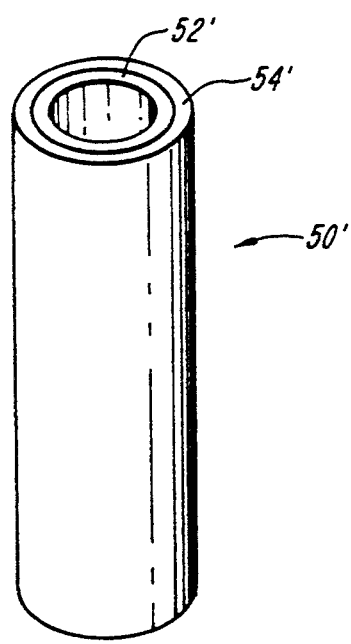
FIGS. 8B and 8C are photomicrographs of tangential sections of a tube formed from the preform of FIG. 8A, taken in the regions corresponding to B and C, respectively, of FIG. 7.

PTFE resin as used in Method 4 was blended in two separate containers with 104 cc and 150 cc, respectively, of Isopar-H per pound of resin. The two resin/lube mixes were then separately poured into a preforming cylinder in concentric layers as shown in FIG. 8A with the inner layer 52' of extrusion preform 50' comprised of higher lube level (150 cc lube/lb) resin and the outer layer 54' of preform 50' comprised of lower lube level (104 cc/lb) resin. As before, a core-rod cylinder was fitted over the core rod of the preforming cylinder to separate the layers during pouring and was removed after pouring was completed. An extrusion preform was then formed by compacting the layers under a pressure of 600 psi.

The preform was then extruded into a 4 mm I.D./5.6 mm O.D. tube in a ram extruder having a reduction ratio of 220:1 in cross-sectional area from preform to extruded tube. Fifteen inch samples were cut from the tubular extrudate and allowed to bake at 300° C. for five minutes prior to stretching in order to remove the extrusion lubricant. The samples were then stretched at a rate of 2.5% per second to a length of 45 inches, followed by sintering by heating the restrained samples to a temperature of 370° C. for four minutes.

Figure 8B:
Figure 8C:
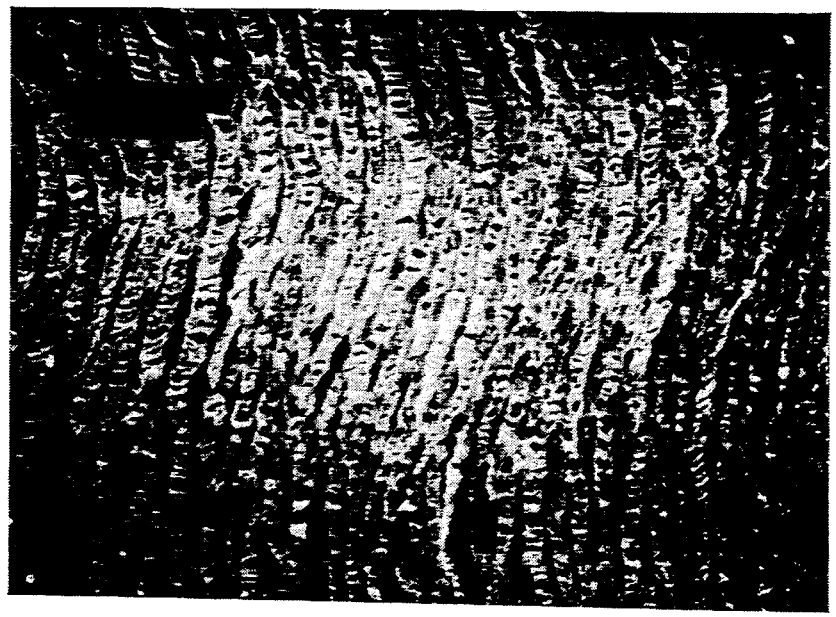

As shown in FIG. 8B, a tangential section at the inner region of a tube so formed has a nodal structure of relatively large, ring-like sheets oriented perpendicular to the tube axis. As indicated in FIG. 8C, the nodal structure at the outer region retains the same orientation, but becomes more closely spaced. Thus, the relative porosity varies, from the inside to the outside, in a sense opposite to that of the tube structure produced by Method 4.

It will be appreciated by those skilled in the art that in each of the foregoing embodiments the structure of nodes and fibrils results in a pore structure wherein interstitial spaces of tapering aspect extend entirely, or substantially entirely through the wall of the tube.

As described above, extrusion from a billet formed with varying levels of lubricant produces a preform, and after stretching results in an article, having a pore structure that varies. Applicant expects a similar effect to result from use of a billet wherein, rather than varying the level of lubricant, one position (e.g., inside, or outside) is formed using a lubricant of different density or a different composition than is used in the other portion. For the example, the preform may be made using a layer of PTFE material mixed with an Isopar-like lubricant, e.g., a simple hydrocarbon solvent of density approximately 0.6, and a layer of the same PTFE material mixed with a heavy oil, such as a more viscous hydraulic pump oil or a glycerin-containing fluid. Following extrusion, both lubricants are baked out, and the final stretched or unstretched article is sintered to fix its microporous structure.

Related effects are also expected when forming a billet wherein one portion has its lubricant less uniformly dispersed in or mixed with the resin. In that case, the voids left upon baking out the lubricant may be expected to result in regions having different nodal size in the coarsely-mixed extrudate than in the well-mixed extrudate. Thus, the invention is understood to include articles formed by extrusion of two different extrusion materials, wherein the materials have the same resin, and differ only in type, quantity, uniformity or other property of the lubricant included in the material.

It will be further understood that while the invention has been described with reference to extrusion of a billet formed of different concentric cylinders to make a tubular item, billets of other shape may advantageously be used to extrude articles of other aspect or shape, such as multi-lumenal solid or perforated bodies as described in applicant's aforesaid co-pending United States patent applications.

Furthermore, a tubular product as described above, may be slit longitudinally to provide a belt-like sheet, and one or more such sheets may be joined or assembled in a multi-layer stack to form an article having through-wall porosities of two or more successive or opposed tapers. In other constructions, a tube as described above may be pressed flat so that it forms a strip two layers thick, with a larger (or smaller) pore structure at its center than at either outside surface.

In addition, as noted above, the invention contemplates the manufacture of articles which have been extruded with a varying lubricant distribution, but not subjected to a stretching or expansion step. These articles have a generally more rigid structure with lower porosity, and do not have the fibril structure characteristic of the expanded product, but may still benefit from the additional control over porosity combined with enhanced microstructure alignment as provided by the present invention, to tailor their mechanical properties.

According to a principal aspect of one presently preferred embodiment of the invention, this structure is employed in a vascular graft, formed of PTFE tube having a lower inside than outside porosity, the variation being introduced by extrusion from a billet having higher outside lube levels, followed by stretching and sintering. Advantageously, the node structure of plate-like sheets oriented perpendicular to the axis of the tube permits deep cellular ingrowth, and provides a flexible anti-kink and non-collapsing lumen structure, yet prevents blood leakage at the smaller-pored wall.

In a proof-of-principle experiment carried out with a tubular prosthesis made in accordance with Method 4 above, the tubes were implanted in the carotid artery of dogs and left in vivo for extended periods to assess patency, cell growth and tissue compatibility. In implants that remained patent, tissue ingrowth had progressed by forty-five days such that morphologically complete normal capillaries had grown through the entire thickness of the tube wall. This single-resin expanded fluoropolymer graft thus appeared to demonstrate, for the first time known to the inventors, an artificial vessel replacement structure essentially capable of supporting natural vessel wall regrowth extending not only along the interior surface, but between the inside and outside surfaces.

It is expected that in other areas where it has historically been possible to achieve tissue growth only for limited times or to limited depths, different forms of prosthesis made in accordance with the above pore-tailoring and uniformity-promoting processes will support enhanced natural or seeded growth of other cell types to form replacement tissue for diverse organs, vessels and tissue structures.

For example, the invention contemplates that an organ prosthesis, partial organ, patch, graft, or organ-like structure be formed of material having the desirable permeability to fluids on a macroscopic scale and porosity to receive cellular growth, possibly in connection with one or more lumena defining flow paths therethrough for carrying blood and/or other biological fluids. For a discussion of a range of shaped porous articles intended for diverse such uses, reference is made to applicant's above-mentioned patent applications. Such shapes may be configured to constitute grafts, intended to patch over and regenerate regions of tissue that have been lost to trauma, disease or surgery, or may constitute entire organs. Furthermore, such prostheses need not be patched into an existing organ, but may, for example, be seeded with culturable cells, cultured and implanted into a well-vascularized region capable of supporting tissue growth and of receiving the material expressed by the tissue for circulating it in the bloodstream. Thus, the inventive prosthesis provides a bioreactor for producing biological material, the walls and lumens serving to sustain the culture and allow exchange of cultured products in the body.

For this latter application, the tailored pore structure of articles of the present invention allows tissue growth and exchange of expressed bioactive materials, without allowing exogenous cells to circulate and without allowing immunity-mediating cells to reach the cultured tissue. The cellular containment thus diminishes the likelihood of inducing a whole body rejection or cell-mediated immune response. By way of example, an artificial pancreas for insulin replacement therapy may be formed by seeding a closed multiluminal article to grow islets of Langerhans, with the cell products and secretions entering blood circulating through one or more of the lumena. In this case, it is desirable to culture the cells and supporting material in vitro, and then implant the functioning culture body to initiate insulin or other replacement therapy. In other examples of this method of use of articles of the present invention, endothelial cells may be cultured to provide their cell products into the bloodstream.

Another class of articles of the present invention having varying pore structure is the class of filters or filtration units. For this application, the presence of a tapering pore structure can be used, for example, in different orientations to prevent particles from reaching and clogging subsurface regions of a filter membrane, or to allow greater fluid pressure through the depth of a filter membrane, in each case having the effect of enhancing overall the filter's lifetime, capacity or filtration rate.

Still another class of articles directly pertaining to the present invention is that of culture beds or bioculture reactors, wherein an extrudate, e.g., a porous tube or sheet made in accordance with the invention, serves as the anchoring structure for cellular material—tissue or microorganisms—that synthesize an enzyme or other substance which is the end product of the process. In this case, the porosity, possibly in a tubular or multilumenal structure may allow the transport of nutrients to one side of the article, and the harvesting of product at another or the same side, without having to break up the cell mat to affect such feeding or harvesting.

Further alterations to the above described embodiments of the invention will be apparent to those skilled in the art and are intended, therefore, to be embraced within the spirit and scope of the invention. That is, the preceding detailed description is intended as illustrative rather than limiting. Accordingly, the invention is to be defined not by the preceding detailed description but by the claims that follow.

What is claimed is:

1. A method of producing a shaped porous article, such method comprising the stops of
    forming a billet of a single fluoropolymer material and a lubricant in which a lubricant concentration gradient has been established along a dimension of the billet,
    extruding the billet to form an extruded article having a shape and a lubricant component concentration that is varied in level corresponding to the concentration gradient of the billet,
    removing lubricant from the article and stretching the extruded article form a porous article with predetermined pore sizes in different regions thereof, wherein larger pores are formed in regions where the extruded article had higher levels of lubricant, and
    sintering the porous article in its stretched state to fix its dimensions
    thereby forming a sintered porous-article of a single fluoropolymer material having different porosities in predetermined regions thereof.

2. The method of claim 1, wherein the step of forming the billet includes forming with a lubricant level that is no lower than about ten percent and no higher than about twenty-four percent.

3. The method of claim 1, wherein the fluoropolymer is a single-resin fluoropolymer.

4. The method of claim 1, wherein the billet is formed with lubricant levels that are selected to provide an article having a pore size distribution that permits tissue growth on at least a portion of the article without permitting fluid leakage through the article.

5. The method of claim 3, wherein the step of sintering is performed to uniformly sinter the porous article at the sintering temperature of said single-resin fluoropolymer.

6. The method of claim 1, wherein the step of forming a billet includes forming a billet in plural layers, at least two layers having different levels of lubricant.

7. The method of claim 1, wherein the step of extruding includes extruding a tubular extruded article.

8. The method of claim 7, wherein the tubular article has a tube axis, and includes a plurality of nodes of flattened aspect oriented transverse to the axis and extending substantially through the tube wall.

9. The method of claim 8, wherein the tubular article has a wall thickness of under about two millimeters.

10. The method of claim 9, wherein the tubular article has a wall thickness of under about one millimeter.

11. The method of claim 10, wherein the tubular article has a wall thickness of about 0.3–0.8 millimeters.

12. The method of claim 11, wherein the step of stretching is performed by stretching at a rate below approximately two percent per second.

13. The method of claim 12, wherein the step of stretching is performed by stretching at a rate below approximately one percent per second.

14. The method of claim 13, wherein the step of stretching is performed by stretching at a rate below approximately one tenth of one percent per second.

15. The method of claim 1, wherein the step of extruding includes extruding a tubular extruded article having a lumen, and the step of stretching includes stretching so as to produce radially-oriented nodes extending about the lumen and interconnected by fibrils, spaces between the nodes defining through channels from said lumen to an outer surface of the article.

16. The method of claim 15, wherein the stretching produces nodes having regions of flattened aspect.

17. The method of claim 1, wherein the step of forming a billet includes forming a billet having different lubricants at different radially disposed positions along its cross-section.

18. The method of claim 17, wherein the different lubricants are lubricants of different density.

19. The method of claim 17, wherein the different lubricants are lubricants of different viscosity.

20. A method of producing a prosthesis, such method comprising the steps of
forming a billet of a single fluoropolymer material having a lubricant concentration gradient across a dimension of the billet corresponding to a desired porosity structure,
extruding the billet to form an extruded prosthesis the extruded prosthesis blank having a distribution of amount of lubrication that varies in correspondence with said concentration gradient of the billet,
removing lubricant from the extruded prosthesis blank and stretching the extruded prosthesis blank to form a porous prosthesis blank the stretching introducing predetermined pore sizes in different regions thereof wherein larger pores are formed in regions where the prosthesis blank had greater amounts of lubricant, and
sintering the porous prosthesis blank in its stretched state to fix its dimensions thereby forming a sintered prosthesis of a single polymer material having different porosities in different regions thereof.

21. The method of claim 20, wherein the lubricant level varies from no less than about ten percent to no more than about twenty-four percent from inside to outside of said billet.

22. The method of claim 21, wherein the prosthesis is a vascular prosthesis and the lubricant level is selected to provide a pore size for tissue growth.

23. The method of claim 22, wherein the porosity structure tapers between inside and outside of the vascular prosthesis.

24. In a method of manufacturing a porous PTFE article having a sintered microporous structure, the improvement comprising forming the article of a single PTFE material mixed with lubricant, wherein a lubricant concentration gradient is established through a cross-section of the article such that the lubricant has different levels at inside and outside, respectively of the article, and stretching the article to achieve a tapered pore structure extending from inside to outside of the article before sintering the article to fix its dimensions, the pore structure extending from smaller pores to larger pores, wherein larger pores are formed in regions where the article has higher levels of lubricant.

25. The method of manufacture of claim 24, wherein the porous PTFE article is a sheet article having a pore size on one surface to define a region of tissue ingrowth, and having a different pore size outside said region.

26. A method of producing a shaped porous article, such method comprising the steps
forming a billet of a single fluoropolymer material and a lubricant in which a lubricant concentration gradient has been established which is a step function along a dimension of the billet,
extruding the billet to form a single-material extruded article having a shape and a lubricant component concentration that differs in level in different regions of the article in accordance with the lubricant concentration gradient of material in the billet,
removing lubricant from the extruded article to form a porous article, and
sintering the porous article thereby forming a sintered porous article having different porosities in different regions thereof, wherein larger pores are formed in regions where the extruded article had higher levels of lubricant.

27. The method of claim 26, further comprising the step of stretching the extruded article prior to sintering.

* * * * *